US006318166B1

United States Patent
Roos

(10) Patent No.: US 6,318,166 B1
(45) Date of Patent: Nov. 20, 2001

(54) METHOD FOR DETERMINING THE MECHANICAL PROPERTIES OF ELONGATED TEXTILE TEST MATERIAL AND A DEVICE FOR CARRYING OUT THE METHOD

(75) Inventor: Gerold Roos, Uster (CH)

(73) Assignee: Lenzing Aktiengesellschaft, Lenzing (AT)

( * ) Notice: Subject to any disclaimer, the term of this patent is extended or adjusted under 35 U.S.C. 154(b) by 0 days.

(21) Appl. No.: 09/145,328

(22) Filed: Sep. 1, 1998

(30) Foreign Application Priority Data

Sep. 2, 1997 (CH) .................................................. 2051/97

(51) Int. Cl.[7] ...................................................... G01L 5/04
(52) U.S. Cl. .............................................. 73/160; 73/828
(58) Field of Search .............................. 73/159, 160, 826, 73/827, 828, 829, 830, 831, 833, 834, 838

(56) References Cited

U.S. PATENT DOCUMENTS

| 4,148,218 |   | 4/1979 | Knowles et al. | 73/829 |
|-----------|---|--------|----------------|--------|
| 4,825,702 | * | 5/1989 | Cizek | 73/828 |
| 4,947,686 | * | 8/1990 | Wendell et al. | 73/159 |
| 5,050,437 | * | 9/1991 | Etter | 73/830 |
| 5,437,182 | * | 8/1995 | Plaschy et al. | 73/160 |
| 5,813,277 | * | 9/1998 | Schmidt et al. | 73/159 |

FOREIGN PATENT DOCUMENTS 43 29 051   3/1995  (DE) .
0 429 376   5/1991  (EP) .
39 42 111   6/1991  (EP) .

OTHER PUBLICATIONS

Stein, H., "Messtechnische Untersuchungen über die Eignung eines neuen Schnellverfahrens zur Ermittlung der Reisskraft von Fortlaufend bewegten Fäden bzw. Gespinsten und Zwirnen", Westdeutscher Verlag Köln, 1966, pp. 37–39.
Stein, H., Tensile Tester for Elastomeric Yarns and Elastic Fabrics STATIMAT EL, Textechno, pp. 2–4.
Chemical Fibers International, vol. 47, Feb. 1997.

* cited by examiner

*Primary Examiner*—Max Noori
(74) *Attorney, Agent, or Firm*—Jacobson Holman, PLLC

(57) ABSTRACT

Mounted within the measuring section (10) formed by two clamping devices (2, 4) are measuring rollers (8, 9) which deflect the test material (10). The deflection results in a force couple (P, P') and a resultant force (R). The resultant force (R) is transferred into a load cell (3) via a link (6). This arrangement enables the clamping devices (2, 4) and the load cell (3) to be mounted separately. The measuring rollers (8, 9) are equipped with incremental transducers (19, 20) by means of which the clamp slippage (Δ1) creeping out of the clamping faces of the clamping devices (2, 4) and the extension of the test material sections (10', 10") are measured.

13 Claims, 3 Drawing Sheets

METHOD FOR DETERMINING THE MECHANICAL PROPERTIES OF ELONGATED TEXTILE TEST MATERIAL AND A DEVICE FOR CARRYING OUT THE METHOD

BACKGROUND OF THE INVENTION

1. Field of the Invention

The present invention concerns a method for the determinating mechanical properties of elongated textile test material, in which the test material is clamped and stretched between two clamping devices and the occurring tensile force is measured.

2. Description of Related Art

Known tensile test equipment for the testing of yarns, twines, narrow tapes and other flexible materials are equipped with two clamping devices. These are mounted vertically one over the other, with a selectable spacing between them. The upper clamping device is connected to a load cell via a rigid connection. The lower clamping device can be moved vertically by means of a drive. A test piece clamped in the clamping devices is subjected to a tensile load by the downward movement of the lower clamping device. The tensile force occurring in the test piece is transmitted to the load cell through the upper clamping device. An incremental transducer connected to the drive records as the extension of the test piece the distance traversed by the lower clamp from the commencement of the test to the breakage of the test piece.

This measuring arrangement is flawed. The coupling of the clamping device and the load cell constitutes a preload on the load cell which impairs its sensitivity. This preload increases the mass inertia and reduces the characteristic frequency of the force measuring system. This influence has a particularly interfering effect if the occurring breaking forces are small in relation to the maximum possible load of the load cell. The test appliances themselves are designed for tensile forces of 500 N to 5 KN and above. This problem is countered with interchangeable load cells and clamping devices. For an extensive range of test material, the breaking forces can extend from a few CN into the range of several KN. The provision of the necessary load cells and clamping devices involves a high level of cost.

A further flaw in the measuring system of this equipment is the fact that the change in the distance between the clamping devices is used for measuring the extension. During a tensile test, the test material is clamped into the clamping devices. The tensile stress prevailing in the test material continues in the direction of pull in both clamping devices and only attains the value zero within the clamping faces. This reduction of tensile force within the clamping faces results in an extension which is not recorded with the measurement method described. The measured extension value is too large.

The actual extension is the change in the distance between the clamps minus twice the "clamp slippage". In the case of test materials with small extension values, this measurement error is negligible, particularly if it is relative to a long clamping length. In the case of elastic test materials with high extension and transverse contraction values, such as rubber-like materials or partially stretched synthetic yarns, or soft-annealed metal wires, this error assumes a magnitude which is no longer negligible. This measurement error is again increased considerably if the clamping length is reduced from the standard value of 500 mm to 100 mm or even 50 mm. Shortened clamping lengths are selected in order to load elastic test materials to breaking point within the greatest possible clamp distance.

The present invention is intended to eliminate the influence of the weight of the clamping device on the force measuring system and the measurement of the clamp slippage is intended to increase the accuracy of the extension measurement.

This object is achieved according to the invention in that the test material between the clamping devices is deflected by an angle and a force couple is formed as a result and in that its resultant force is used for determination of the strength properties.

SUMMARY OF THE PRESENT INVENTION

A preferred embodiment of the method according to the invention is characterised in that the extension of the test material including the clamp slippage is converted into signals which are proportional to the extension and that these signals are evaluated.

The invention further concerns a device for execution of the said method, with a fixed and a displaceable clamping device between which a measuring section is created. The device according to the invention is characterised in that at least one free-running measuring roller is disposed within the measuring section for the purpose of deflecting the test material by the said angle.

A preferred embodiment of the device according to the invention is characterised in that two measuring rollers are provided, at least one of which is connected to a load cell.

According to the invention, the clamping device is separated from the load cell. For the purpose of force transfer, a measuring roller with an inbuilt incremental transducer is mounted on the load cell. The load cell measuring roller and a second measuring roller are mounted within the test section in such a way that the test material is deflected on the two measuring rollers. Consequently, the test section with the test material between the clamping devices has a trapezoidal shape.

The load cell, together with the measuring roller, is mounted below the upper clamping device. The second measuring roller, which is likewise equipped with an incremental transducer, is mounted in the proximity of the lower displaceable clamping device. During the test process, the test material is clamped into the clamping devices and deflected via the two measuring rollers. Here, the angle of contact of the test material on the measuring roller connected to the load cell is of particular importance. The test material subject to tensile force and bearing on this measuring roller forms a force couple. The angle formed by the force couple determines the magnitude of the resultant force that is transferred into the load cell via the measuring roller. By setting the contact angle between 0° and 60°, it is possible to use load cells of which the maximum load is significantly lower than the tensile force to be tested. If the selected contact angle is 60° (enclosed angle 120°), then the resultant force corresponds to the tensile force in the test material. In the case of the measurement arrangement described, both the length of material between the clamps and the distance between the measuring rollers can be defined as the clamping length to which the extension values are related. In all cases, it is the length of material between the clamping devices including the deflection via the two measuring rollers that is defined as the measuring length.

During the test process, the test material is stretched between the clamps by a constant increase of the distance between the clamps. The change in the clamp device spacing between the commencement of the test and the breakage of the test material is measured as the extension value. This change in spacing is measured by an incremental transducer connected to the drive for the movable clamping device and is transmitted to the evaluator as a value which is proportional to the extension. The extension components of the material pieces which are outside the vertical test section, including the clamp slippage, set the measuring rollers in rotation. The incremental transducers built into the measuring rollers likewise convert the rotational angles of the two measuring rollers into values which are proportional to the extension and transmit them to the evaluator.

The extension, related to the selected reference length, is calculated in the evaluator on the basis of the extension values transmitted by the incremental transducers and the time-related progression of these values. Further test parameters and characteristics of the measured test material can be determined by inclusion of the tensile forces measured by the load cell during the test and the time-related change in these tensile forces.

DESCRIPTION OF THE DRAWINGS

The invention is described more fully below with reference to an embodiment example and drawings, wherein are depicted.

DESCRIPTION OF EMBODIMENTS PREFERRED AT THE TIME OF FILING FOR THIS PATENT

Figure 1:
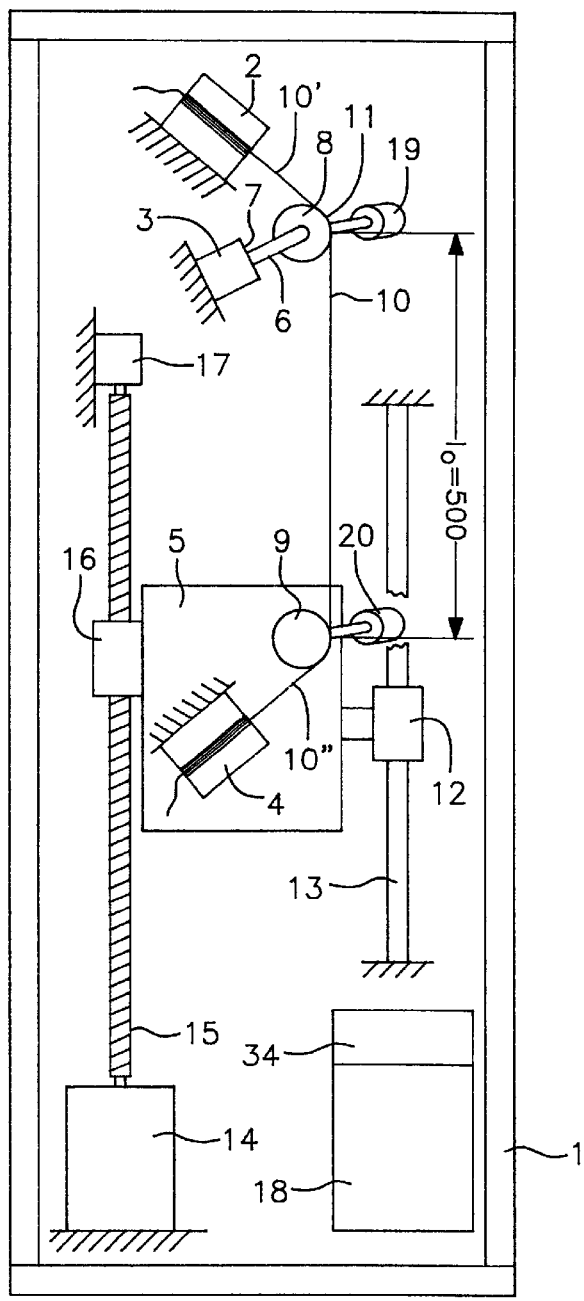
FIG. 1 a simplified, schematic representation of a breaking force testing device, FIG. 2 a section from FIG. 1, with closely spaced clamping devices, FIGS. 3a and 3b sectional representations through the clamping gap of a clamping device, with the origination and progression of the clamp slippage at the start (FIG. 3a) and during a test process (FIG. 3b), FIG. 4 the force couple formed by the test material on the upper measuring roller, with the resultant force, FIG. 5 a view of the upper measuring roller with a load cell and measuring roller cover, and FIG. 6 a section through one of the two measuring rollers with a cover and incremental transducer.

FIG. 1 depicts a simplified view of a breaking force testing device. The modules necessary for application of the load and for measuring the breaking force and the extension of the test material are disposed on the front of the cabinet-type housing 1. Functional modules which are not relevant to the invention have been omitted.

The fixed upper clamping device 2 and the load cell 3 are mounted independently of one another in the upper part of the front of the appliance. The displaceable clamping device 4 is attached to a slide 5. For the purpose of transferring the tensile force to the load cell 3, a freely rotating measuring roller 8 is mounted on a link 6 which is attached to the force transfer face 7 of the load cell 3, a further measuring roller 9 being mounted on a movable slide 5. The clamping devices 2 and 4 and measuring rollers 8 and 9 are mounted and aligned in such a way that the test material 10 is guided through the test course in a trapezoidal formation. Test material subjected to tensile load forms a couple of forces P; P' of equal magnitude at the contact point 11 on the measuring roller 8. The resultant force R is transferred into the load cell 3 via the link 6. In general, the angle a of the force couple determining the resultant force R is selected so that the force component R acting upon the load cell 3 is 10% to 100% of the tensile force P.

The slide 5 carrying the lower clamping device 4 and the second measuring roller 9 is guided on the bar 13 by a slide block 12. The slide 5 can be vertically displaced by the motor 14, the threaded spindle 15 and the nut 16 attached to the slide 5. Mounted at the end of the threaded spindle 15 which is distant from the motor 14 is an incremental transducer 17 which, by means of the controller 18, controls the movement of the clamping length $l_0$. During a test, the enlargement of the clamp spacing from the commencement of a test to the breakage of the test piece, which is interpreted as the extension, is measured by the incremental transducer 17 in the form of pulses which are proportional to the displacement. The displacement measured thus corresponds to the total extension of the test material, including the clamp slippage creeping out of the clamping devices 2, 4.

The extension components of the test material sections 10' and 10" effect a rotational movement of the measuring rollers 8 and 9. Incremental transducers 19 and 20 connected to the measuring rollers 8 and 9 measure the rotational valuation of the measuring rollers 8 and 9 and convert this into pulses which are proportional to the extension. Both the magnitude and the timerelated progression of the extension values of the incremental transducers 17, 19 and 20 are stored in the evaluator 34. The extension values are determined by means of an evaluation program following the breakage of the test material $l_0$ or following the conclusion of a test series.

Figure 2:
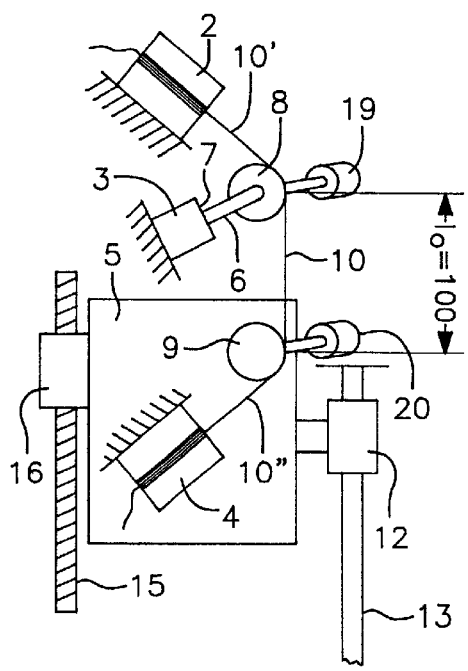

FIG. 2 shows a section from FIG. 1 with a greatly shortened clamping length $l_0=100$ mm. This shows that the test material sections 10' and 10" and the measurement of the test force have remained the same. The accuracy of the extension measurement is significantly improved in the case of short clamping lengths by the measurement of the clamp slippage creeping out of the clamping devices 2 and 4.

Figure 3A:
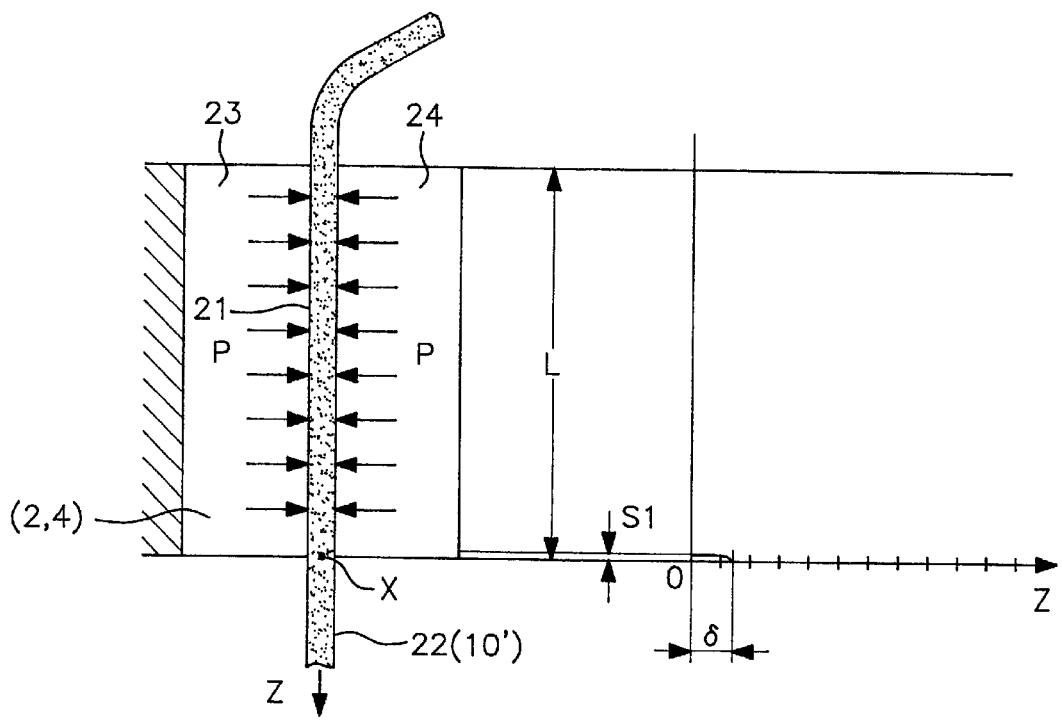
Figure 3B:
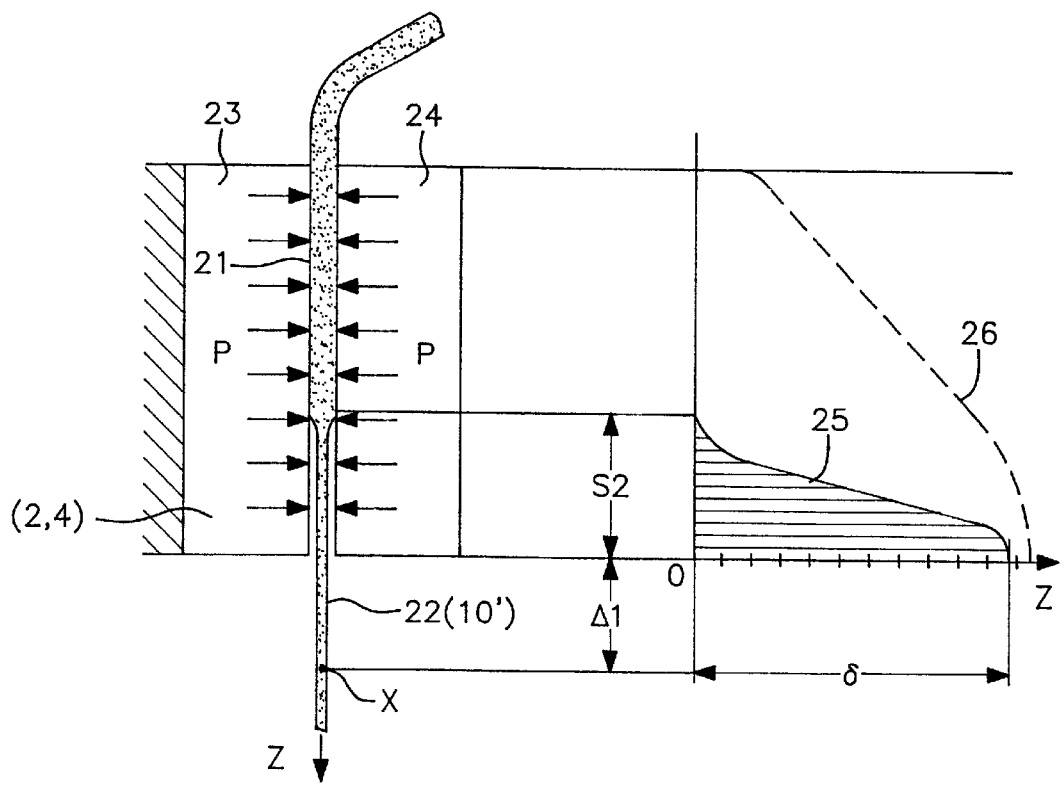

FIGS. 3a and 3b show sectional representations through the clamping gap 21 of a clamping device 2, 4, with the origination and progression of the clamp slippage.

FIG. 3a shows the clamping gap 21 at the start of a test operation. The test material 22 is located between the fixed clamping jaw 23 and the movable clamping jaw 24. The clamping force P is evenly distributed over the clamping length L. Z denotes the tensile force prevailing in the test material 22. X is a mark applied to the test material 22 shortly after commencement of application of the load. The stress σ resulting from the tensile force Z and the clamp slippage $S_1$ is plotted on an accompanying graph.

FIG. 3b shows the clamping gap 21 shortly before the breakage of the clamped test material 22. The tensile force Z and the resultant extension Δ1 have caused the test material 22 to contract. Over the section $S_2$ the tensile force Z has reduced from a maximum value of Z to zero. This reduction of force within the clamping section results in a clamp slippage Δλ. The mark X previously applied at the exit from the clamping gap 21 has moved away from the clamping jaws 23, 24 by the amount Δ1. The accompanying graph shows the stress curve 25 within the clamping gap 21. The broken graph line 26 represents the case of slippage of the test material 22 through the clamping gap 21. The tensile force Z and the stress σ do not attain the values Z=0, σ=0 respectively until after the clamping gap 21.

Figure 4:
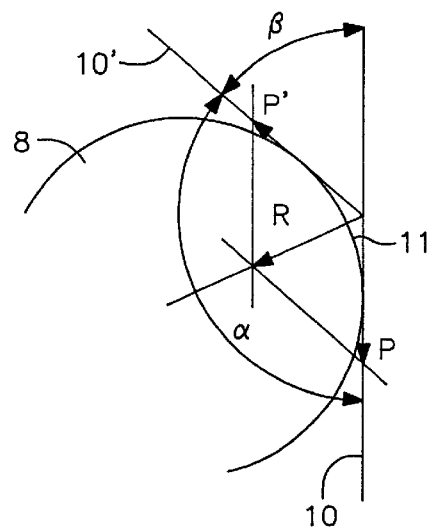

FIG. 4 shows the force couple P, P' formed on the upper measuring roller 8 with the resultant force component R used for measuring the tensile force Z. The test material sections 10 and 10' contact the upper measuring roller 8 and form the enclosed angle α. P and P' are the tensile forces prevailing in the test material 10 and R is the resultant force component transferred into the load cell 3, the vector direction being maintained. The angle β corresponds to the deflection angle.

Figure 5:
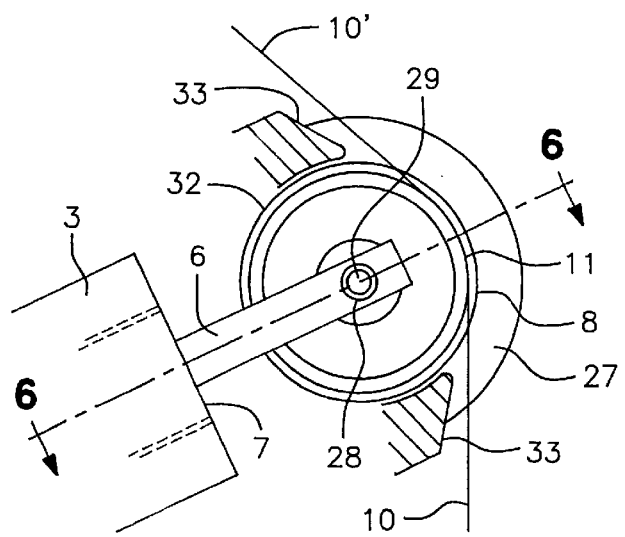

FIG. 5 shows a view of the upper measuring roller 8 with a load cell 3 and a cover 27. The measuring roller 8, which is mounted by means of a ball bearing 28, is connected to the force transfer face 7 of the load cell 3 via the link 6 and shielded by the cover 27 as protection against the penetration of material residues and dust. The intake slants 33 are fashioned so that the test material 10 to be measured is guided exclusively by the measuring roller 8 and so that, following breakage of the test material 10, the recoiling end of the material cannot damage the measuring roller 8.

Figure 6:
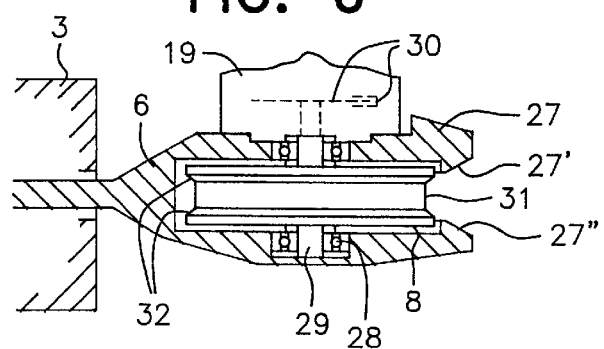

FIG. 6 shows a section along the line A—A of FIG. 5. An incremental transducer 19, consisting of an incremental disc and scanning unit 30, is mounted on the shaft 29 which is mounted in ball bearings 28. The running face 31 of the measuring roller 8 has bevelled flanges 32 on both sides which prevent the test material from slipping off while it is being inserted in the test section. The two bevelled cover parts 27', 27" form a contactless labyrinth seal between the measuring roller 8 and the cover 27 and prevent the penetration of dust and material residues.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realised that changes are possible within the scope of this invention and it is further intended that each element or step recited in any of the following claims is to be understood as referring to all equivalent elements or steps. The following claims are intended to cover the invention as broadly as legally possible in whatever form it may be utilised. The invention claimed herein is new and novel in accordance with 35 U.S.C.§ 102 and satisfies the conditions for patentability in § 102. The invention claimed herein is not obvious in accordance with 35 U.S.C. § 103 and satisfies the conditions for patentability in § 103. This specification and the claims that follow are in accordance with all of the requirements of 35 U.S.C. § 112.

What is claimed is:

1. A method for determining mechanical properties of an elongated textile test material, said method comprising the steps of:
   clamping and stretching the elongated textile test material between two clamping devices and measuring the occurring tensile force,
   deflecting the elongated textile test material by an angle between the clamping device,
   converting extension of the elongated textile test material, including clamp slippage, into signals which are proportional to the extension, and
   evaluating said signals.

2. A method according to claim 1, characterized in that the resultant force of a force couple formed due to the deflection of the test material between the clamping devices is used for determination of mechanical properties.

3. A device for determining mechanical properties of an elongated textile test material, said device comprising a fixed and a movable clamping device between which a measuring section is formed, at least one free-running measuring roller disposed within the measuring section for the purpose of deflecting the elongated textile test material by an angle, at least one of the measuring rollers being equipped with an incremental transducer by which an extension of the elongated textile test material in the measuring section located between the clamping device and the at least one measuring roller, including clamp slippage of the elongated textile test material creeping out of the clamping devices, which is transferred to the measuring rollers as rotational movement, is converted into signals which are proportional to the extension.

4. A device according to claim 3, wherein two measuring rollers are provided, at least one of which is connected to a load cell.

5. A device according to claim 4, wherein at least one measuring roller is connected to a load cell via a link.

6. A device according to claim 5, wherein the link acts in a vector direction of the resultant force and the resultant force is transferred to a force transfer face of the load cell via the link.

7. A device according to claim 3, wherein an incremental transducer is provided to monitor the change in the distance between the clamping devices and the extension values measured by the incremental transducer are converted into signals which are proportional to the extension and are delivered to an evaluator together with the signals of the incremental transducer which are proportional to the extension.

8. A device according to claim 3, wherein the at least one measuring roller has a cover provided with guide faces for deflecting recoiling ends following breakage of the elongated textile test material.

9. A device according to claim 4, wherein the at least one measuring roller has a cover provided with guide faces for deflecting the recoiling ends following the breakage of the elongated textile test material.

10. A device according to claim 5, wherein the at least one measuring roller has a cover provided with guide faces for deflecting the recoiling ends following the breakage of the elongated textile test material.

11. A device according to claim 6, wherein the at least one measuring roller has a cover provided with guide faces for deflecting the recoiling ends following the breakage of the elongated textile test material.

12. A device according to claim 3, wherein the at least one measuring roller has a cover provided with guide faces for deflecting the recoiling ends following the breakage of the elongated textile test material.

13. A method for determining mechanical properties of an elongated textile test material, said method comprising the steps of:
   clamping and stretching the elongated textile test material between two clamping devices and measuring the occurring tensile force,
   deflecting the elongated textile test material by an angle between the clamping devices and forming a force couple as a result and using a resultant force for a determination of the mechanical properties of the elongated textile test material, and
   converting extension of the elongated textile test material, including clamp slippage, into signals which are proportional to the extension, and
   evaluating said signals.

* * * * *